(12) United States Patent
Jaradat

(10) Patent No.: US 7,252,434 B2
(45) Date of Patent: Aug. 7, 2007

(54) RADIATION THERAPY MACHINE CALIBRATION APPARATUS PROVIDING MULTIPLE ANGLE MEASUREMENTS

(75) Inventor: Hazim Ahmed Jaradat, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 204 days.

(21) Appl. No.: 11/081,159

(22) Filed: Mar. 16, 2005

(65) Prior Publication Data
US 2006/0219945 A1   Oct. 5, 2006

(51) Int. Cl.
*A61B 6/04* (2006.01)
(52) U.S. Cl. .................... 378/207; 378/65; 378/175
(58) Field of Classification Search ............... 378/207, 378/64, 65, 167, 172, 174, 175
See application file for complete search history.

(56) References Cited

U.S. PATENT DOCUMENTS 5,511,107 A    4/1996  Sliski
6,364,529 B1   4/2002  Dawson
6,405,072 B1   6/2002  Cosman
6,493,574 B1   12/2002 Ehnholm et al.
6,712,508 B2   3/2004  Nilsson et al.
6,974,254 B2 * 12/2005 Paliwal et al. .............. 378/207

FOREIGN PATENT DOCUMENTS

WO    WO 00/29871    5/2000

OTHER PUBLICATIONS

Paliwal, Bhudatt, et al., A spiral phantom for IMRT and tomotherapy treatment delivery verification, Med. Phys. 27 (11) Nov. 2000, 2000 Am. Assoc. Phys. Med.

* cited by examiner

*Primary Examiner*—Kiet T. Nguyen
(74) *Attorney, Agent, or Firm*—Boyle Fredrickson Newholm Stein & Gratz S.C.

(57) ABSTRACT

A phantom for rotational radiation therapy machines allows beam fluence and energy to be measured at a variety of beam angles without intervening adjustment of the phantom. The phantom in the preferred embodiment provides two half cylinders directed along the axis of rotation of the machine abutting about a common center.

35 Claims, 2 Drawing Sheets

RADIATION THERAPY MACHINE CALIBRATION APPARATUS PROVIDING MULTIPLE ANGLE MEASUREMENTS

STATEMENT REGARDING FEDERALLY SPONSORED RESEARCH OR DEVELOPMENT

This invention was made with United States government support awarded by the following agencies: NIH CA088960. The United States has certain rights in this invention.

CROSS-REFERENCE TO RELATED APPLICATIONS

- - -

BACKGROUND OF THE INVENTION

The present invention relates to phantoms for use with radiation therapy equipment and in particular to a phantom providing improved quality assurance measurement of radiation therapy machines operating in a rotational mode.

External beam radiation therapy treats cancer in a patient by means of variable energy radiation beams directed through a patient's skin to the site of the tumor. Normally, the tumor is treated with number of beams, each at different angles, the beams converging on the tumor site to increased effect while reducing exposure at the skin and other normal tissue in the path of the beams.

Intensity modulated radiation therapy (IMRT) machines may employ an increased number of beams to provide a uniform dose the tumor. To increase the uniformity and the conformity of the dose to the target, arc beams are used to deliver radiation from a throughout a continuous range of angles, as in the case of conventional radiation treatment machines, or in a helical fashion as used by the Hi-Art tomotherapy machine. The intensity of multiple rays within the beam is varied over the angular range to produce a radiation dose distribution that conforms closely to tumors especially for targets of complex shapes.

It is important that all radiation therapy machines be checked regularly to ensure that the correct dose is provided for treating the tumor. Daily quality assurance measurements may be performed by placing a radiation detector such as an ionization chamber on the patient table of the radiation therapy machine and directing the radiation beam downward toward the ionization chamber. The beam is directed through blocks of attenuating material approximating the characteristics of tissue, and measured with two thicknesses of attenuating material to deduce radiation energy. The fluence and energy are compared to target values for the machine.

The angle of the radiation beam can affect the beam characteristics as an indirect result of variations in gravitational load on the machine components including the linear accelerator. The increased dose accuracy and large number of angled beams used in IMRT makes measurement of the beams at other than vertical angles and while the beam is rotating important. Normally, the characteristics of the treatment beam are measured with the beam in a vertical position.

BRIEF SUMMARY OF THE INVENTION

The present invention provides a phantom that may be conveniently used for daily measurements of radiation over almost the full angular range of the beam. The phantom further allows for energy measurement without time consuming manual modifications of the phantom. The result is a phantom that is fast and convenient to use and which provides additional data about beam quality over the continuous angular range of beam directions.

Specifically, the present invention provides a test apparatus for radiation therapy machines providing radiation beams at multiple angles. The test apparatus includes a radiation attenuating material positioned to have a portion radially symmetric within a vertical plane. An electronic radiation detector is placed in the radiation attenuating material at an axis centered with respect to the symmetry of the radially symmetric portion. The radiation detector is monitored by a monitoring device to provide measurements of a radiation beam at multiple angles within the vertical plane.

Thus, it is an object of at least one embodiment of the invention to provide a test apparatus that can easily measure radiation characteristics at angles other than vertical and without the need for manually changing the setup.

The test apparatus may include a stand for holding the axis of the radiation attenuating material at an isocenter of the radiation therapy machine at which radiation beams at multiple angles intersect.

Thus it is another object of at least one embodiment of the invention to allow a series of measurements at different beam angles to be made by running the radiation therapy machine and without repositioning of the test apparatus.

The stand may be such as to rest on the patient table with the patient table in its substantially lowest position.

Thus it is another object of at least one embodiment of the invention to reduce the shadow of the patient table on the phantom so as to increase the angular range at which the unobstructed radiation beam may be measured.

The symmetric portion of the radiation attenuating material may be a portion of a cylinder.

Thus it is another object of at least one embodiment of the invention to provide a simple surface that places a constant thickness of material between the detector and the radiation beam for a variety of beam angles.

The radiation attenuating material may be a portion of two hemi-cylindrical selectors having different diameters and joined along a diameter to have a common axis.

Thus it is another object of at least one embodiment of the invention to provide a shape that creates two effective thicknesses of material in the radiation beam during rotation of the gantry to provide for the automatic collection of energy data.

The two sectors may be symmetric about a vertical axis.

It is thus another object of at least one embodiment of the invention to provide comparable angular effects in the two radiation beams that will be combined for energy measurements. To the extent that gravitational effects on the radiation beam mechanism will be similar for angles that are equally displaced about the vertical axis, this vertical configuration of the phantom provides improved comparisons for energy measurement purposes.

The radiation attenuating material may be a solid material mimicking water, for example, Solid Water®.

Thus it is another object of at least one embodiment of the invention to provide a consistent attenuation material that is simple to handle.

The detector may be a coaxial ionization detector.

It is thus another object of at least one embodiment of the invention to provide a simple commercially available detector that is naturally rotationally symmetric in its sensitivity.

The invention may include a computer receiving data from the test apparatus to compute fluence and energy for radiation beams at different beam angles. These may be output as a table or graph of radiation characteristics as a function of beam angle.

It is thus another object of at least one embodiment of the invention to provide improved information about the beam as a function of angle.

The radiation attenuating material may include indicia indicating a point centered along the axis of the test apparatus. For example, the indicia may provide lines in three orthogonal planes centered at the point on the axis.

Thus, it is object of at least one embodiment of the invention to allow simple alignment of the apparatus in three dimensions with the radiation therapy machine isocenter using the laser markers typically associated with the radiation therapy equipment.

These particular objects and advantages may apply to only some embodiments falling within the claims and thus do not define the scope of the invention.

DETAILED DESCRIPTION OF THE PREFERRED EMBODIMENT

Figure 1:
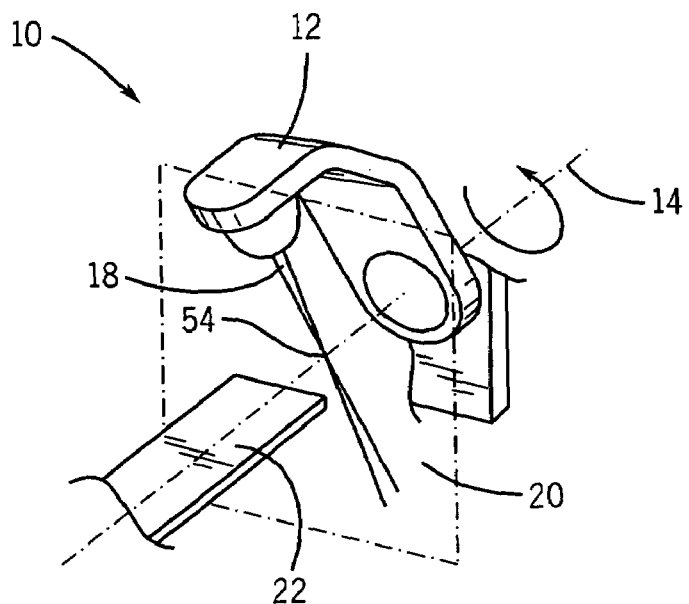
FIG. 1 is a simplified perspective view of a radiation therapy system for delivering radiation at a plurality of beam angles within a vertical plane and about an isocenter and showing a patient table for supporting a patient during treatment.

Referring now to FIG. 1, a radiation therapy machine 10 provides a gantry 12 rotating about a generally horizontal axis of rotation 14 for delivering a beam 18 of radiation at a variety of beam angles within a vertical plane 20. During treatment, the gantry 12 rotates about a patient (not shown) supported on a patient table 22 extending across the vertical plane 20 and parallel to the axis of rotation 14. An isocenter 54 is defined where the beam 18 crosses the axis of rotation 14.

Figure 2:
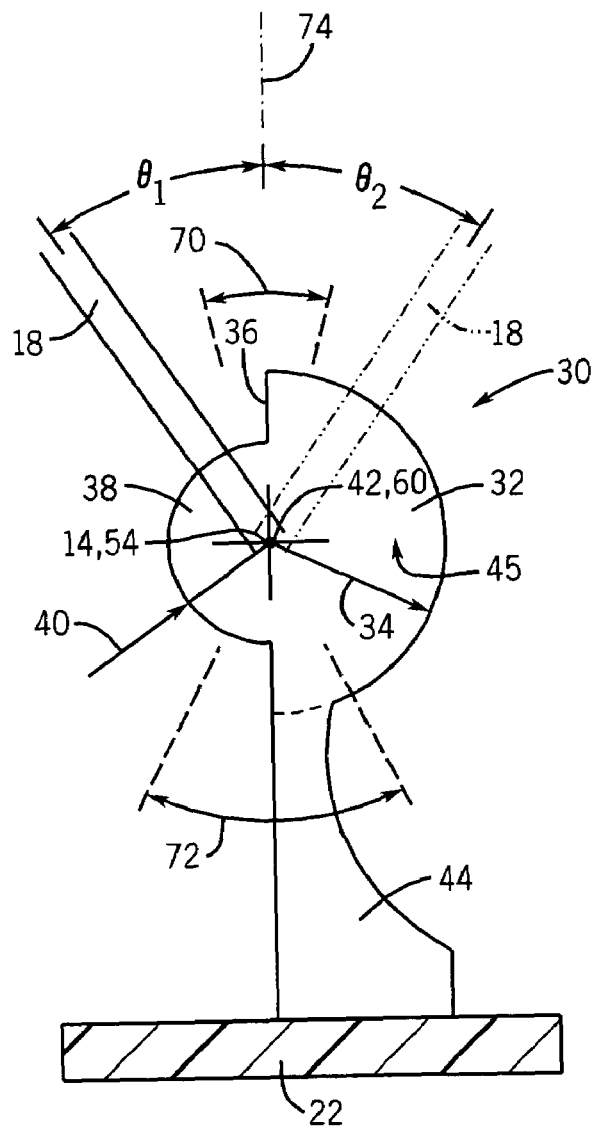
FIG. 2 is a front elevational view of the phantom of the present invention as may be supported on the table of FIG. 1 at the isocenter.

Referring now to FIG. 2, the present invention provides a phantom 30 suitable for use with the radiation therapy machine 10 of FIG. 1. In the preferred embodiment, the phantom 30 provides a first hemi-cylinder 32 ten centimeters in radius 34 and six centimeters thick. Its diametric face 36 is oriented vertically and abuts a second hemi-cylinder 38 having a five-centimeter radius 40 and six centimeters thick. Both hemi-cylinders 38 and 32 have common axes 42 being the axes of the cylinders of which they are portions. The hemi-cylinders 32 and 38 thus present outer peripheries that are piece-wise radially symmetric about the axes 42.

The lower edge of hemi-cylinder 32 is supported on a stand 44 selected so that when the patient table 22 is in a lower-most position, the axes 42 of the phantom 30 may be aligned with axis of rotation 14, and the hemi-cylinders 32 and 38 centered on the isocenter 54.

The material of the hemi-cylinders 32 and 38 is selected to have an electron density equivalent to that of water and may be made of Solid Water®, a material available commercially from Gammex of Middleton, Wis. The stand may be made of an arbitrary material, but conveniently may also be made of Solid Water® material.

Figure 3:
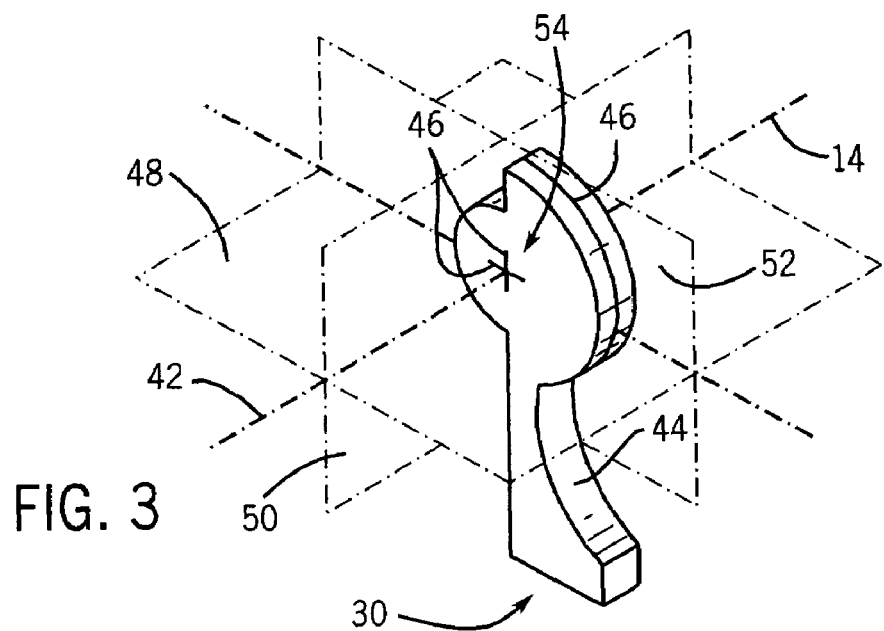
FIG. 3 is a perspective view of the phantom of FIG. 2, showing its alignment with three orthogonal planes intersecting at the machine's isocenter as defined by machine associated lasers.

Referring to FIG. 3, a front face 45 of the hemi-cylinders 32 and 38 are scribed with vertical and horizontal lines 46 intersecting at the axes 42. These lines 46 may be aligned with lines projected by laser projectors scanning a horizontal plane 48 and vertical plane 50 intersecting the axis of rotation 14 and typically associated with the radiation therapy machine 10. The outer periphery of hemi-cylinder 32 and or 38 may have a vertically scribed line 46 that may align with vertical plane 52 also established by a laser projector so that the phantom 30 may be readily positioned on axis of rotation 14 with isocenter 54 centered within the phantom 30 along axes 42.

Figure 4:
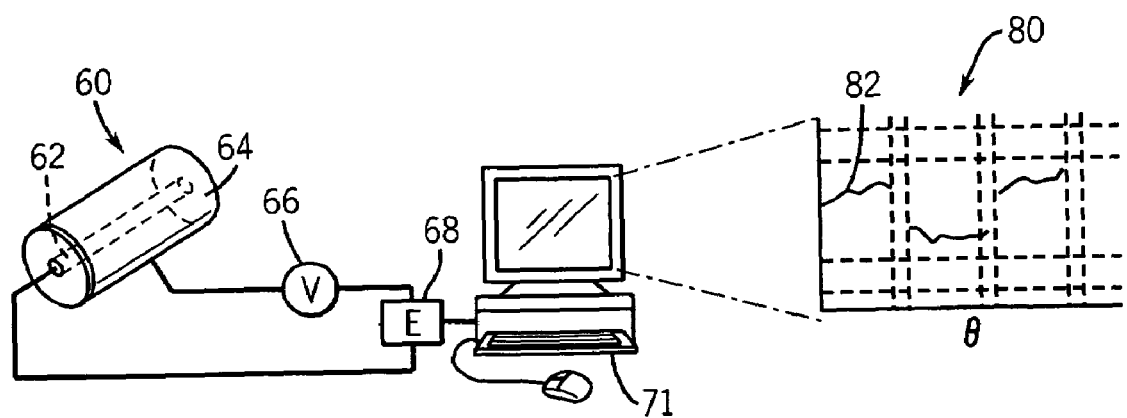
FIG. 4 is a perspective view of an ionization detector used with the phantom of FIGS. 2 and 3 and a block diagram showing the collection of data from that detector for the display of data in graphical form.

Referring now to FIGS. 2 and 4, an ionization detector 60 having a cylindrical center electrode 62 coaxially within an outer tubular electrode 64 may be embedded in the phantom 30 at, and aligned with, axes 42. The ionization detector may be, for example, a PTW ion chamber commercially available from CNMC Company, Inc. of Nashville, Tenn.

A voltage is imposed between the center electrode 62 and the outer tubular electrode 64 of the ionization detector 60, by voltage source 66, and the integrated current flow measured by electrometer 68. As is understood in the art, the current flow provides a measurement of the ionization of gas inside the ionization detector 60 by radiation and thus of the fluence of the radiation passing through the ionization detector 60. The electrometer 68 may provide data directly to an electronic computer 71 which may be programmed to produce a number of output formats as will be described.

Referring now to FIG. 2 in use, the phantom 30 is aligned with the axes 42 at the isocenter 54 and the radiation therapy machine 10 programmed to produce a beam approximately ten centimeters wide (along the vertical plane 20) and five centimeters deep (in the inferior/superior direction along the axis of rotation 14). The gantry 12 is set to rotate at a known speed, for example, one minute per rotation, and the phantom 30 is exposed to the radiation beam 18 as the gantry 12 rotates.

As the gantry 12 rotates, the beam 18 may continuously illuminate the phantom except at two sectors 70 and 72 when the beam is turned off. Sector 70 encompasses a range of about 20 degrees on each side of vertical 74 so that the downward directed beam 18 does not illuminate the discontinuity in radius of the phantom 30 for these near vertical angles of beam 18. Conversely, sector 72 encompasses a range of about 80 degrees so that the upwardly directed beam 18 is not shadowed by the table 22. During these periods, the beam is blocked by the multi-leaf-collimator (MLC) and the value of the electrometer 68 stays at its last value until the beam 18 is again unblocked.

The ionization detector 60 will detect radiation projected at the phantom 30 over a range of angles θ and regularly spaced readings are taken of the electrometer 68, for example, every thirty seconds. Three complete rotations are completed in the preferred embodiment. The electrometer could also be set to collect the current from the ionization chamber resulting in a instantaneous rotational output of the beam for two different depths.

Measurements at these regular time intervals with a known gantry speed will yield three measurements of beam fluence for beams passing through each side of the phantom 30, the measurements attenuated by either hemi-cylinder 38 or by hemi-cylinder 32. So, for example, the following information may be collected:

| TIME | ELECTROMETER READING |
|------|----------------------|
| 30   | 22.87                |
| 60   | 41.29                |
| 90   | 64.22                |
| 120  | 82.71                |
| 150  | 105.72               |
| 180  | 124.22               |

With the gantry 12 started at its bottom most position and beam 18 directed upward along vertical 74 and proceeding in a clockwise direction, the first reading will represent measurements through the hemi-cylinder 38 of approximately 180 degrees minus one-half of the sectors 70 and 72. The second reading of the next 30 seconds corresponds to an angle of measurement through hemi-cylinder 32. Similarly, the next four readings of 90, 120, 150 and 180 will represent repeated measurements alternating between hemi-cylinder 38 and 32. Because the phantom does not need to be adjusted during the acquisition of energy data, rapid measurements may be made of output and energy.

The total dose can be determined and compared to a target dose for the machine. Deviation by less than a fixed percent (e.g., 2 percent) is verified.

The contribution of fluence for each half scan of hemi-cylinder 38 or 32 can be easily extracted by subtraction to yield the following values:

| Hemi-Cylinder 38 | Hemi-Cylinder 32 |
|------------------|------------------|
| 22.87            | 18.42            |
| 22.93            | 18.49            |
| 22.01            | 18.50            |

Averages may be derived from these fluence readings. These averages may be divided to deduce an energy value, in this example 0.805, which may be compared to a predetermined target value, in this example 0.811. Again a deviation between actual and target values is determined.

The data through each hemi-cylinder 32 and 38 is taken at mirror image angle ranges about the vertical 74, thereby nullifying possible energy variations caused by fluence variation with beam angle.

It will be understood that the ionization detector 60 may also provide instantaneous measurement values during rotation of the gantry which may be displayed on a computer 71 as a chart 80 providing for dose or energy 82 as a function of gantry angle. In this case, energy is determined by comparing instantaneous beam measurements at angles $\theta_1$ and $\theta_2$ that are mirror images about the vertical 74 again nullifying possible energy variations caused by fluence variation with beam angle.

The information collectible by this phantom 30 may be processed to yield a variety of additional information. For example, periodicity in fluence as a function of angle may be used to evaluate the gantry rotational speed by noting a phase shift in fluence over the three revolutions. Multi-Leaf latency deviations may also be deduced by inconsistency in the readings obtained on the two sides of sectors 70 and 72.

It is specifically intended that the present invention not be limited to the embodiments and illustrations contained herein, but include modified forms of those embodiments including portions of the embodiments and combinations of elements of different embodiments as come within the scope of the following claims.

I claim:

1. A test apparatus for radiation therapy machines providing radiation beams at multiple angles, the test apparatus comprising:
    a radiation attenuating material positionable to have a portion radially symmetric about an axis in a vertical plane;
    an electronic radiation detector placed in the radiation attenuating material at the axis; and
    a monitor communicating with the electronic radiation detector to provide radiation measurements of a radiation beam of the radiation therapy machine at multiple angles of the radiation beam.

2. The test apparatus of claim 1 further including a stand for holding the electronic radiation detector centered with the axis at an isocenter of the radiation therapy machine at which radiation beams at multiple angles intersect.

3. The test apparatus of claim 2 wherein the stand is sized to be supported on top of a patient table with the axis at the isocenter of the radiation therapy machine when the table is in a substantially lowest position.

4. The test apparatus of claim 1 wherein the portion of the radiation attenuating material is a portion of a cylinder.

5. The test apparatus of claim 4 wherein the radiation attenuating material is at least a portion of two hemi-cylindrical sectors having different diameters and joined along a diameter to have a common axis of symmetry at the axis.

6. The test apparatus of claim 5 wherein the diameters are oriented vertically.

7. The test apparatus of claim 5 wherein the diameters differ by an amount suitable to deduce radiation energy from reading of beams collected through different of the hemi-cylindrical sectors.

8. The test apparatus of claim 1 wherein the radiation attenuating material has radiation transmitting properties mimicking water.

9. The test apparatus of claim 8 wherein the mimicking water is Solid Water.

10. The test apparatus of claim 1 wherein the detector is a coaxial ionization detector.

11. The test apparatus of claim 1 wherein the detector is a coaxial ionization detector.

12. The test apparatus of claim 11 further providing an output of radiation characteristics as a function of beam angle.

13. The test apparatus of claim 12 further providing a semi-continuous graph of radiation characteristics as a function of beam angle.

14. The test apparatus of claim 12 wherein the output compares fluence at different beam angles to a predefined standard.

15. The test apparatus of claim 12 wherein the output compares energy at different beam angles to a predefined standard.

16. The test apparatus of claim 1 wherein the radiation attenuating material includes indicia indicating a point centered on the axis.

17. The test apparatus of claim 16 wherein the indicia are lines in three orthogonal planes centered at the point on the axis of symmetry.

18. A test apparatus for radiation therapy machines providing radiation beams at multiple angles within a vertical plane, the test apparatus comprising:

a radiation attenuating material positionable within the vertical plane to have at least two different portions providing a different thickness of attenuating material between a center axis of the radiation attenuating material and an edge of the radiation attenuating material in the vertical plane at different of a plurality of angles within the vertical plane;

an electronic radiation detector placed in the radiation attenuating material at the center axis; and a monitoring device communicating with the electronic radiation detector for providing radiation measurements of a radiation beam of the radiation therapy machine at multiple angles of the radiation beam.

19. The test apparatus of claim 18 further including a stand for holding the electronic radiation detector centered with the center axis at an isocenter of the radiation therapy machine at which radiation beams at multiple angles intersect.

20. The test apparatus of claim 18 wherein the portion is a portion of a cylinder.

21. The test apparatus of claim 20 wherein the radiation attenuating material is at least a portion of two hemi-cylindrical sectors having different diameters and joined along a diameter to have a common axis of symmetry at an axis.

22. The test apparatus of claim 21 wherein the diameters differ by an amount suitable to deduce radiation energy from reading of beams collected through different of the hemi-cylindrical sectors.

23. The test apparatus of claim 18 wherein the radiation attenuating material has a radiation transmitting properties mimicking water.

24. The test apparatus of claim 23 wherein the mimicking water is Solid Water RTM.

25. The test apparatus of claim 18 wherein the detector is a coaxial ionization detector.

26. The test apparatus of claim 18 further including a computer receiving data from the test apparatus to compute fluence and energy for radiation beams at different beam angles.

27. The test apparatus of claim 26 further providing an output of radiation characteristics as a function of beam angle.

28. The test apparatus of claim 27 further providing a semi-continuous graph of radiation characteristics as a function of beam angle.

29. The test apparatus of claim 27 wherein the output compares fluence at different beam angles to a predefined standard.

30. The test apparatus of claim 27 wherein the output compares energy at different beam angles to a predefined standard.

31. The test apparatus of claim 18 wherein the radiation attenuating material includes indicia indicating a point centered on the center axis.

32. The test apparatus of claim 31 wherein the indicia are lines in three orthogonal planes centered at the point on the axis of symmetry.

33. A method of testing a radiation therapy system providing radiation beams at multiple angles within a vertical plane using a test apparatus having a radiation attenuating material positionable within the vertical plane to have at least two different portions providing a different thickness of attenuating material between a center axis of the radiation attenuating material and an edge of the radiation attenuating material in the vertical plane at different of a plurality of angles within the vertical plane, and an electronic radiation detector placed in the radiation attenuating material at the center axis, the method comprising the steps of:

(a) positioning the test apparatus with the center axis at an isocenter of the radiation therapy system at which different radiation beams at multiple angles intersect;

(b) operating the radiation therapy system to expose the test apparatus to radiation beams at different angles through the different thicknesses of attenuation material; and (c) deducing energy of the radiation beams by comparing outputs of the electronic radiation detector for comparable beams through different thicknesses.

34. The method of claim 33 further including the step of outputting the energy at different beam angles.

35. The method of claim 33 further including the step of outputting the energy as a graph as a function of beam angle.

* * * * *